United States Patent [19]

Kucheria et al.

[11] Patent Number: 4,613,516
[45] Date of Patent: Sep. 23, 1986

[54] BONDING OF BIOACTIVE GLASS COATINGS

[75] Inventors: Chhattar S. Kucheria, Mystic; Rodney E. Wells, Groton, both of Conn.

[73] Assignee: Pfizer Hospital Products Group, Inc., New York, N.Y.

[21] Appl. No.: 699,972

[22] Filed: Feb. 8, 1985

[51] Int. Cl.$^4$ .......................... A01N 1/02; B05D 3/02
[52] U.S. Cl. ........................................ 427/2; 427/330; 427/376.4; 427/376.5; 427/427
[58] Field of Search .................. 427/376.4, 376.5, 318, 427/330, 2, 327, 427

[56] References Cited

U.S. PATENT DOCUMENTS

| | | | |
|---|---|---|---|
| 2,842,458 | 7/1958 | Feeney et al. | 427/376.5 |
| 3,061,449 | 10/1962 | Hoffman | 427/376.5 |
| 4,044,170 | 8/1977 | Scharbach et al. | 427/2 |
| 4,159,358 | 6/1979 | Hench et al. | 427/318 |
| 4,221,824 | 9/1980 | Leonard et al. | 427/376.5 |
| 4,234,972 | 11/1980 | Hench et al. | 427/318 |
| 4,478,904 | 10/1984 | Ducheyne et al. | 427/2 |

Primary Examiner—Sadie L. Childs
Attorney, Agent, or Firm—Charles J. Knuth; Peter C. Richardson; Gezina Holtrust

[57] ABSTRACT

The adherence of a bioactive glass coating to a metal substrate is improved by applying said glass to said substrate in admixture with at least one of cobaltic oxide, cobaltous oxide, nickel oxide or manganese oxide, and firing the coated substrate at at least about 730° C.

9 Claims, No Drawings

BONDING OF BIOACTIVE GLASS COATINGS

BACKGROUND OF THE INVENTION

The present invention relates to a method of bonding biologically active (hereafter called "bioactive") glass coatings to metal substrates, particularly medical prostheses, and to a metal substrate coated with bioactive glass.

Bioactive glasses for coating of metal substrates suitable for prostheses or surgical implants are known in the art, e.g. U.S. Pat. No. 4,234,972. A method is disclosed allowing use of glasses and metals which do not have closely matched coefficients of thermal expansion.

Matching coefficients of thermal expansion are required when conventional coating methods are used requiring high firing temperatures. On subsequent cooling, thermomechanical stress in the glass layer is reduced when thermal expansion coefficients match so avoiding cracks in the glass coating.

It is an object of the invention to increase the bond strength between the glass and the metal by developing a chemical bond between the glass and the metal on firing the glass-coated metal substrate at high temperature. In view of the high firing temperatures matching thermal expansion coefficients are essential.

SUMMARY OF THE INVENTION

The invention is concerned with a method of bonding a bioactive glass coating to a metal substrate comprising applying to said metal substrate said bioactive glass in admixture with at least one metal oxide selected from the group consisting of cobaltic oxide, cobaltous oxide, nickel oxide and manganese oxide, and firing the coated substrate at a temperature of at least about 730° C., said bioactive glass having substantially the same coefficient of expansion as said metal substrate.

The invention is also concerned with a metal substrate coated with an admixture of a bioactive glass and at least one metal oxide selected from the group consisting of cobaltic oxide, cobaltous oxide, nickel oxide and manganese oxide, said bioactive glass having substantially the same coefficient of expansion as said metal substrate.

The metal oxide used in the invention is preferably cobaltic oxide ($CO_2O_3$) or cobaltous oxide (CoO) or an equimolar mixture thereof ($CO_3O_4$). The metal oxide is generally applied in an amount of about 0.2–3.0% based on the dry bioactive glass.

DETAILED DESCRIPTION OF THE INVENTION

According to the invention, any bioactive glass may be used having the same coefficient of expansion as the metal substrate to which it is applied. Bioactive glasses on reaction with body fluids form a seris of surface reactive films bonding living tissue such as bone to the glass. Suitable bioactive glasses include those having the following composition by weight:

| | |
|---|---|
| $SiO_2$ | 40–60% |
| $Na_2O$ | 10–32% |
| CaO | 10–32% |
| $P_2O_5$ | 0–12% |
| $CaF_2$ | 0–18% |
| $B_2O_3$ | 0–20% |

Specific bioactive glasses include the following:

| | |
|---|---|
| $SiO_2$ | 43–48% |
| $Na_2O$ | 18–21% |
| CaO | 19–22% |
| $B_2O_3$ | 4–15% |
| $P_2O_5$ | 4–10% |

More specifically, the following bioactive glasses are included:

| (1) Composition | % by weight |
|---|---|
| $SiO_2$ | 44.65 |
| $Na_2O$ | 20.01 |
| CaO | 19.59 |
| $B_2O_3$ | 10.30 |
| $P_2O_5$ | 5.45 |

The thermal expansion coefficient of this composition is $13.43 \times 10^{-6}/°C$.

| (2) Composition | % by weight |
|---|---|
| $SiO_2$ | 43.83 |
| $Na_2O$ | 18.41 |
| CaO | 21.63 |
| $B_2O_3$ | 10.11 |
| $P_2O_5$ | 6.02 |

The thermal expansion coefficient of this composition is $13.31 \times 10^{-6}/°C$.

| (3) Composition | % by weight |
|---|---|
| $SiO_2$ | 47.45 |
| $Na_2O$ | 19.48 |
| CaO | 21.60 |
| $B_2O_3$ | 5.45 |
| $P_2O_5$ | 6.02 |

The thermal expansion coefficient of this composition is $13.12 \times 10^{-6}/°C$.

Suitable metals for the metal substrate include any metal from which an artificial prosthesis may be manufactured. Examples of suitable metals include steels such as surgical stainless steel and carbon steel, cobalt-chrome alloys such as cobalt-chrome-molybdenum alloys, titanium, titanium alloys, noble metals such as platinum, and noble metal alloys. Vitallium (trademark) alloy is a preferred alloy and consists of:

| Element | % by weight |
|---|---|
| Carbon | 0.25 |
| Silicon | 0.75 |
| Manganese | 0.70 |
| Chromium | 28.00 |
| Molybdenum | 5.50 |
| Cobalt | 64.80 |

The thermal expansion coefficient of cast Vitallium is $13.21 \times 10^{-6}/°C$. substantially matching those of the above three compositions.

The bioactive glass compositions are made by usual methods for making glasses involving mixing of the ingredients, melting and then cooling.

The bioactive glass composition is admixed with cobaltic oxide, cobaltous oxide, nickel oxide or manganese oxide, or suitable mixtures of such oxides. The mixing is conveniently by preparing a slurry of the glass and adding the metal oxide to the slurry. The slurry typically contains small particles of mean size of about 0.0065 mm of the bioactive glass, a liquid such as ethanol or acetone, and an emulsifier. Alternatively, the metal oxide may be melted together with a melt of the bioactive glass.

The admixture of glass and metal oxide is applied to the metal substrate by conventional methods. Usually, the application is by spray-coating at room temperature, with a slurry such as described above.

The metal substrate is often treated to increase adherence of the glass coating to the substrate. Suitable treatment includes oxidation and roughening of the substrate surface, e.g. as described in U.S. Pat. No. 4,159,358 which is hereby incorporated by reference.

The metal substrate surface is usually cleaned, preferably ultrasonically in methanol, and dried such as by gentle blow-drying with a particle-free aerosol. After optional oxidation or roughening, the glass-metal oxide slurry is applied by spray-coating. Suitably, an airbrush is used at a distance of 3.5 inches at 10 psi and variable angles to ensure uniform coating.

After application of the glass-metal oxide slurry, the alloy is allowed to dry before firing. The firing is at a temperature of at least 730° C., and usually not higher than 760° C. Below 730° C. and above 760° C., the bond between the substrate and the coating tends to be less satisfactory.

The adherence of the glass to the metal is tested by holding one end of a glass coated metal strip in a vise and the other end of the strip in a vise grip. On twisting the strip by about 10°, the strip and the coating are examined visually and microscopically. In the test, the glass coating will break due to the mechanical stress caused by the twisting action. Depending on the strength of the glass metal bond, the glass coating may become entirely detached from the metal strip evidencing no glass metal bond, or the glass coating may partly or entirely adhere to the metal strip even though the glass coating itself breaks under the stress of the test.

The following examples illustrate the invention.

EXAMPLE 1

(Comparative)

A slurry was prepared containing the following:

| | |
|---|---|
| Ethanol (95%) | 112.00 g |
| Butvar ® B-76 resin | 1.67 g |
| Triton ® N-150 emulsifier | 0.83 g |
| Bioactive glass (2) above | 55.00 g |

Butvar B-76 resin is polyvinylbutryl resin.
Triton N-150 emulsifier is liquid nonylphenoxy polyethoxy ethanol.

The bioactive glass is glass composition (2) described above. The glass particles had a mean particle size of 0.0053 mm.

After the mixing for 24 hours, the slurry was spray coated at ambient temperature on a strip of Vitallium that had first been roughened, cleaned and then oxidized. The coating was dried under ambient conditions and then fired at up to 732° C. in air for one minute.

The strip was tested for adherence by the above adherence test. The glass coating separated in a layer leaving behind a shiny white metal surface without any glass remaining adhered to the metal. Thus, the glass coating had a very poor adherence to the metal.

EXAMPLE 2

The glass slurry (20 g) prepared in Example 1 was mixed with 0.15 g cobaltic oxide ($Co_2O_3$) resulting in a net cobaltic oxide content of 2.31% based on the weight of the dry glass. After mixing for 24 hours, the slurry was spray coated at ambient temperature on pre-roughened preoxidized Vitallium strips. The strips were dried and fired as described in Example 1. The formed glass strips were tested for adherence. As a result of the test, the glass coating fractured. However, the glass coating fragments remained adhered to the metallic strip. Addition of $Co_2O_3$ thus increased the adherence of glass to metal.

EXAMPLE 3

A slurry was prepared containing the following:

| | |
|---|---|
| Ethanol (95%) | 150.0 g |
| Butvar B-76 resin | 2.24 g |
| Triton N-150 emulsifier | 1.11 g |
| Bioactive glass (2) above | 75.0 g |
| Mixture of cobaltous oxide and cobaltic oxide ($Co_3O_4$) | 0.75 g |

The bioactive glass had a mean particle size of 0.0056 mm and contained 1% cobalt oxide on a dry glass basis. A preoxidized Vitallium strip was coated with the slurry as described in Example 2 and tested for adherence. The glass coating broke. Some of the glass coating became detached from the strip so adherence was not as good as in Example 2.

EXAMPLE 4

A glass slurry was prepared as in Example 3 except that 0.75 g $Co_2O_3$ was substituted for 0.75 g $Co_3O_4$. The cobalt oxide content of the slurry remained 1% based on the dry glass.

The glass coated strips were prepared in a similar manner as in Example 1 and tested for adherence. The glass coating broke and the coating fragments remained adhered to the metal strip showing very good adherence. Fewer and smaller bubbles were observed than in Example 2.

EXAMPLE 5

Two parts of the slurry of Example 3 were mixed with one part of the slurry of Example 4 for 24 hours. The cobalt oxide content of the slurry was 0.67% $Co_3O_4$ and 0.33% $Co_2O_3$ based on the dry glass.

Glass coated strips were prepared as in Example 1 and tested for adherence. The glass coating broke and fragments thereof remained adhered to the metal strip showing very good adherence. The glass coating contained very few bubbles.

I claim:

1. A method of bonding a bioactive glass coating to a metal substrate comprising applying to said metal substrate a slurry containing a mixture of said bioactive glass and at least one metal oxide selected from the group consisting of cobaltic oxide, and cobaltous oxide, and firing the coated substrate at a temperature of at least about 730° C., said bioactive glass having substantially the same coefficient of expansion as said metal substrate.

2. A method as claimed in claim 1 wherein said metal oxide is cobaltic oxide.

3. A method as claimed in claim 1 wherein said metal oxide is cobaltous oxide.

4. A method as claimed in claim 1 wherein said metal oxide is a mixture of cobaltous oxide and cobaltic oxide.

5. A method as claimed in claim 1 wherein said metal oxide is applied in a range of about 0.2–3.0% based on the weight of the dry bioactive glass.

6. A method as claimed in claim 1 wherein said bioactive glass is applied by spray-coating.

7. A method as claimed in claim 1 wherein said metal substrate is dried after application of said bioactive glass.

8. A method as claimed in claim 1 wherein said metal of said metal substrate is a cobalt-chromium-molybdenum alloy.

9. A method as claimed in claim 1 wherein said mixture of bioactive glass and metal oxide is in the form of an ethanol slurry.

* * * * *